United States Patent
Sigrist et al.

(10) Patent No.: US 6,780,980 B1
(45) Date of Patent: Aug. 24, 2004

(54) PROCESS FOR THE MODIFICATION OF SURFACE

(75) Inventors: Hans Sigrist, Kernenried (CH); Yann Chevolot, Ecublens (CH); David Crout, Coventry (GB); Jose Martins, Braga (PT); Hans-Jörg Mathieu, La Croix s/Lutry (CH); Dieter Lohmann, Münchenstein (CH)

(73) Assignee: Centre Suisse d'Electronique et de Microtechnique S.A. (CH)

( * ) Notice: Subject to any disclaimer, the term of this patent is extended or adjusted under 35 U.S.C. 154(b) by 50 days.

(21) Appl. No.: 09/606,040

(22) Filed: Jun. 29, 2000

(30) Foreign Application Priority Data

Jun. 30, 1999 (EP) .............................. 99112422

(51) Int. Cl.[7] .............................. C07H 17/00
(52) U.S. Cl. .................................... 536/18.5
(58) Field of Search .................. 530/5; 435/6; 436/524, 436/518; 422/177

(56) References Cited

U.S. PATENT DOCUMENTS

| | | | |
|---|---|---|---|
| 5,154,808 A | * 10/1992 | Miyasaka et al. | 204/157.15 |
| 5,308,460 A | * 5/1994 | Mazid et al. | |
| 5,563,056 A | * 10/1996 | Swan et al. | 435/180 |
| 5,858,802 A | * 1/1999 | Chai-Gao et al. | 436/524 |

FOREIGN PATENT DOCUMENTS

| | | | |
|---|---|---|---|
| EP | 0 124 676 | 11/1984 | |
| WO | WO 91/16425 | * 10/1991 | C12N/11/06 |
| WO | WO 96/31557 | * 10/1996 | C08J/7/18 |

OTHER PUBLICATIONS

Leonard et al. ("ToF–SIMS and XPS Study of Photoactivatable Reagents Designed for Surface Glycoengineering", Surface and Interface Analysis, 26, pp. 793–799, 1998).*

Chevolot et al. ("Synthesis and Characterization of a Photoactivatable Glycoaryldiazirine for Surface Glycoengineering", Bioconjugate Chem. 10, pp. 169–175, 1998).*

* cited by examiner

Primary Examiner—Kenneth R. Horlick
(74) Attorney, Agent, or Firm—Parkhurst & Wendel, L.L.P.

(57) ABSTRACT

The present invention relates to a process for the modification of a material surface comprising the steps of ($a_1$) photochemically fixing one or more different compounds of formula

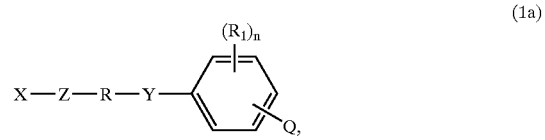

(1a)

onto the material surface, or ($a_2$) photochemically fixing a compound of formula

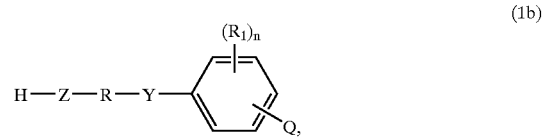

(1b)

onto the material surface and subsequently converting the —ZH groups to —Z—X moieties, wherein the variables each have the meanings as given in the claims; and (b) enzymatically attaching one or more further carbohydrates to the X radicals of the modified surface obtained according to stop ($a_1$) or ($a_2$). The materials obtainable by the process of the invention are useful, for example, for the manufacture of biomedical devices including biosensors.

16 Claims, No Drawings

PROCESS FOR THE MODIFICATION OF SURFACE

The present invention relates to a process for the modification of material surfaces with carbohydrates, and articles, in particular biomedical articles or biosensors comprising said modified surfaces.

Materials when in contact with biological fluids will undergo numerous phenomena such as protein adsorption, cell/material interaction or host response. In order to get a good integration of medical devices one wants to reduce non-specific adsorption and favor specific interaction of a desired cell type to achieve a controlled response [of the living medium]. This is also the case for biosensors. Since all cells are covered with a dense coating of sugars, it has long been predicted that oligosaccharides must be critical determinants of cell-cell communications. Molecules that interact with cell-attached oligosaccharides are in particular receptor proteins or carbohydrates. However, biologically relevant recognition of such proteins or carbohydrates on the surface of a biomedical article or biosensor requires an oligosaccharide modified surface in a specialized fashion; in particular the oligosaccharides should have a proper spacing and density as well as the proper three-dimensional shape on the material. Although methods to physically or chemically immobilizing carbohydrates on a material surface are already known, surfaces obtained by these processes so far have not proven satisfactory to provide effective cell-cell interactions. Accordingly, there is a demand for an improved process for the immobilization of oligosaccharides on a material surface which makes it possible to produce oligosaccharide patterns on a material surface that provide effective interactions with proteins, carbohydrates and the like.

The present invention therefore in one embodiment relates to a process for the preparation of a carbohydrate structure on a material surface comprising the steps of:

($a_1$) photochemically fixing one or more different compounds of formula

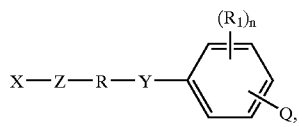
(1a)

onto the material surface, wherein X is the radical of a mono- or oligosaccharide, R is a divalent organic radical having from 2 to 30 C-atoms which may be further substituted, Z is —O—, —S— or a direct bond, Y is a functional group linking R to the aromatic ring, $R_1$ is an electron-withdrawing substituent and n is an integer from 0 to 4, Q is a radical of formula

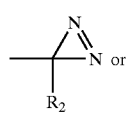
(2a)

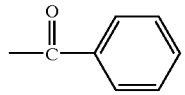
(2b)

and $R_2$ is an electron-withdrawing substituent; or ($a_2$) photochemically fixing a compound of formula

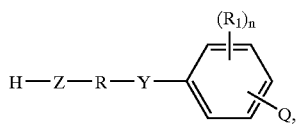
(1b)

wherein R, $R_1$, n, Y, Z and Q are as defined above, onto the material surface and subsequently converting the —ZH groups to —Z—X moieties, wherein X has the above meaning; and (b) enzymatically attaching one or more further carbohydrates to the X radicals of the modified surface obtained according to step ($a_1$) or ($a_2$).

The variable X is advantageously the radical of a mono-, di-, tri- or tetrasaccharide, which in case of an oligosaccharide may be linear or branched. In one embodiment of the invention X is the radical of a mono- or disaccharide and in particular the radical of a disaccharide. Examples of preferred carbohydrate radicals X are a galactose, lactose, mannose, N-acetyl glucosamine, N-acetyl galactosamine or N-acetyl lactosamine and in particular a galactose or lactose. In another embodiment of the invention X is a tetrasaccharide, in particular a branched tetrasaccharide.

Z is preferably a group —S—.

Suitable meanings of R are, for example, linear or branched $C_2$–$C_{30}$-alkylene which is unsubstituted or substituted, for example, by hydroxy, and is uninterrupted or interrupted, for example, by —O— or —$NR_3$— wherein $R_3$ is hydrogen or $C_1$–$C_4$-alkyl; $C_1$–$C_{12}$-alkylene-$C_8$–$C_{10}$-arylen or $C_1$–$C_{12}$-alkylene-$C_6$–$C_{10}$-arylen-$C_1$–$C_{12}$-alkylene, for example $C_1$–$C_{12}$-alkylene-phenylene or $C_1$–$C_{12}$-alkylene-phenylene-$C_1$–$C_{12}$-alkylene; $C_1$–$C_{12}$-alkylene-$C_5$–$C_8$-cycloalkylene, for example $C_1$–$C_{12}$-alkylene-cyclohexylene; $C_1$–$C_{12}$-alkylene-$C_5$–$C_8$-cycloalkylene-$C_1$–$C_{12}$-alkylene, for example $C_1$–$C_{12}$-alkylene-cyclohexylene-$C_1$–$C_{12}$-alkylene; or $C_1$–$C_{12}$-alkylene-heterocyclene or $C_1$–$C_{12}$-alkylene-heterocyclene-$C_1$–$C_{12}$-alkylene, wherein the heterocyclyl ring is each, for example, five- or six-membered, contains at least one N—, O— or S-atom and in addition may comprise one or more carbonyl groups, for example $C_1$–$C_{12}$-alkylene-succinimidylene or N,N-di-$C_1$–$C_{12}$-alkylene-piperazinylene.

R is advantageously linear or branched $C_2$–$C_{24}$-alkylene, preferably linear or branched $C_4$–$C_{18}$-alkylene and most preferably linear $C_8$–$C_{10}$-alkylene, which in each case may be interrupted by —O— or —$NR_3$—, and wherein $R_3$ is hydrogen or $C_1$–$C_4$-alkyl. R is most preferably a linear alkylene radical which is uninterrupted or interrupted by —O—.

Y is, for example, a functional group —C(O)—, —OC(O)—, —C(O)$NR_4$—, —$NR_4$C(O)—, —OC(O)—NH—, —NHC(S)NH— or —NHC(O)NH—, wherein $R_4$ is hydrogen or $C_1$–$C_4$-alkyl. Y is preferably a group —C(O)$NR_4$— wherein $R_4$ is hydrogen, and the amino group is bonded to the phenyl ring.

$R_1$ is, for example, fluorine or trifluoromethyl, n may be an integer from 0 to 4 and is preferably 0.

Q is a group of formula (2b) or preferably of formula (2a) above.

An example of a preferred radical $R_2$ is trifluoromethyl.

A preferred group of compounds of formulae (1a) and (1b) corresponds to the formulae

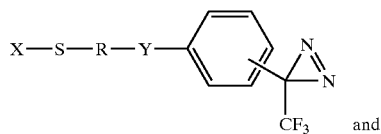 (1a')

and

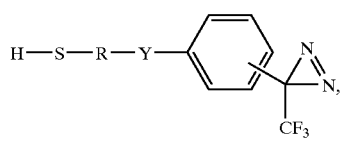 (1b')

wherein X is the radical of a mono-, di-, tri- or tetrasaccharide, R is linear or branched $C_4$–$C_{18}$-alkylene, Y is a functional group —C(O)O—, —OC(O)—, —C(O)NR$_4$—, —NR$_4$C(O)—, —OC(O)—NH—, —NHC(S)NH— or —NHC(O)NH—, wherein $R_4$ is hydrogen or $C_1$–$C_4$-alkyl.

The compounds of formula (1a) or (1a') may be prepared, for example, by reacting a compound of the above formula (1b) or (1b'), for example after activating the thiol group by silylation, with a mono- or oligosaccharide corresponding to the radical X using, for example, $ZnI_2$ as a catalyst. Another synthetic route comprises reacting a compound of the above formula (1b) or (1b') with a mono- or oligosaccharide corresponding to the radical X, wherein the hydroxy group to be converted previously has been activated, for example, with trichloroacetimidate and the remaining hydroxy groups have been protected, for example by acetylation, at a temperature of, for example, room temperature, and finally deprotecting the hydroxy groups of the carbohydrate by a treatment in an acidic medium or preferably with a base such as an alkali alkoxide.

A further synthetic route for the preparation of the compounds of formula (1a) comprises first of all preparing a compound of formula

X'—Z—R—Y$_1$    (3), wherein Z and R are as defined above, X' corresponds to the above mono- or oligosaccharide radical X in a form wherein the hydroxy groups are protected, for example by acetylation, and $Y_1$ is a functional group, for example a carboxy, hydroxy or amino group —NHR$_4$, reacting said compound of formula (3) with a compound of formula

 (4)

wherein Q, $R_1$ and n are as defined above, and $Y_2$ is a functional group that is coreactive with $Y_1$, for example hydroxy, an amino group —NHR$_4$ or an isocyanato or isothiocyanato group, and finally deprotecting the hydroxy groups of the carbohydrate radical X' by a treatment with a base as mentioned before.

The compounds of formula (3) may be obtained, for example, by reaction of a mono- or oligosaccharide corresponding to the radical X wherein some or all of the hydroxy groups have been protected, for example by acetylation, with a compound of formula

HZ—R—Y$_1$    (5), wherein, Z, R and $Y_1$ are as defined above, in the presence of a Lewis acid such as $BF_3$ etherate at a temperature of, for example, room temperature.

The compounds of formula (4) and (5) are known or may be obtained according to methods known in the art.

The compounds of formula (1b) or (1b') may be obtained, for example, by reacting a compound of the above formula (4) with a compound of the above formula (5).

Still a further synthetic route for the preparation of the compounds of formula (1a) comprises reacting a compound of formula

X—ZH    (6), wherein Z is —S— and X is as defined above, with a compound of formula

 (7)

wherein Q, $R_1$, Y and n are as defined above, and R' is a divalent organic radical having from 2 to 30 C-atoms which carries a C—C double bond.

The compounds of formula (6) are known or can be obtained according to methods known in the art. The compounds of the formula (7) may be obtained, for example, as described in A. Collioud et al., Bioconjugate Chemistry 4, 528–536 (1993).

Suitable materials onto which the compounds of formula (1a) or (1b) may be fixed, are, for example, quartz, ceramics, glasses, silicate minerals, silica gels, metals, metal oxides, carbon materials such as graphite, diamond, or glassy carbon, natural or synthetic organic polymers, or laminates, composites or blends of said materials. Some examples of polymers are polyaddition and polycondensation polymers (polyurethanes, epoxy resins, polyethers, polyesters, polyamides and polyimides); vinyl polymers (polyvinyl alcohols, polyacrylates, polymethacrylates, polystyrene, polyethylene and halogenated derivratives thereof, polyvinyl acetate and polyacrylonitrile); elastomers (silicones, polybutadiene and polyisoprene); or modified or unmodified biopolymers (collagen, cellulose, chitosan and the like).

One group of suitable materials useful for applying a carbohydrate structure on the surface comprises inorganic materials, e.g. ceramic, quartz, diamond, diamond-like carbon, conductive carbon, polysilicon, silicium dioxide, tantalium oxide, silicium nitride, titanium dioxide, titanium carbide or silicium carbide or metals, such as silicon, Another group of suitable materials useful for applying a carbohydrate structure on the surface comprises organic polymers, e.g. polystyrene.

The compounds of formulae (1a) or (1b) may be applied to the material surface in step ($a_1$) or ($a_2$) according to processes known per se. For example, the material surface to be treated is immersed in a solution of the compound of formula (1a) or (1b), or a layer of the compound of formula (1a) or (1b) is first of all deposited on the material surface, for example, by dipping, spraying, spreading, knife coating, pouring, rolling, spin coating or vacuum vapor deposition. Specific surface patterning may be accomplished, for example, by mask-assisted contact printing, ink-jet printing or micro-contact printing of a compound of formula (1a) or (1b) onto a material surface. The fixation of the compound of formula (1a) or (1b) on the material surface then may be initiated by irradiation, particularly by UV radiation. Suitable light sources for the irradiation are known to the artisan and comprise for example mercury lamps, high pressure mercury lamps, xenon lamps, carbon arc lamps or sunlight. The time period of irradiation may depend for example on the desired pattern of carbohydrates on the surface and the light intensity employed but is usually in the range of up to 60 minutes, preferably from 1 to 30 minutes, and particularly preferably from 5 to 25 minutes. It may be advantageous to carry out the irradiation in an atmosphere of inert gas.

After the photochemical fixation of the compound of formula (1a) or (1b), any non-covalently bonded carbohydrate compound can be removed, for example by treatment with suitable solvents.

In case that a compound of formula (1b) has been fixed onto the surface according to step ($a_2$), the —Z—H groups being present on the thus modified surface are subsequently converted to —Z—X groups by methods known in the art, for example as mentioned above.

In step (b) the attachment of a further carbohydrate onto the mono- or oligosaccharide modified surface obtained according to step ($a_1$) or ($a_2$) occurs advantageously by reacting the carbohydrate with the mono- or oligosaccharide units that are already immobilized on the surface in the presence of an enzyme, in particular in the presence of a glycosyltransferase. Step (b) thus comprises the transfer of a glycosyl group from a donor to an acceptor by means of a specific glycosyl transferase. The donor is suitably an enzyme substrate which is activated with the glycosyl group to be transferred, e.g. a nucleoside. The terminal sugar radicals present on the modified surface obtained according to step ($a_1$) or ($a_2$) function as acceptor molecules.

The further carbohydrate to be enzymatically attached is preferably a mono- or disaccharide, preferably a monosaccharide. Examples of suitable monosaccharides to be attached in step (b) are glucose, galactose, N-acetyl glucosamine, N-acetyl galactosamine, fucose, mannose, sialic acid or xylose, in particular glucose or sialic acid.

Glycosyltransferases suitable to aid selectively attaching a carbohydrate, for example the above-mentioned carbohydrates, to an acceptor saccharide are known to the art-skilled worker and can be taken from textbooks of enzyme chemistry, for example from D. Schomburg, D. Stephen (Eds.), Enzyme Handbook 12. Class 2.3.2–2.4, Transferases, Springer Berlin, Heidelberg, New York, Tokyo 1996. The textbook discloses i.a. suitable sialyl transferases, galactosyl transferases, fucosyl transferases, mannosyl transferases, glucosyl transferases or xylosyl transferases.

Suitable reaction media and conditions, for example appropriate enzyme substrates and other optional ingredients such as proteins, buffers and the like are known to the art-skilled worker or conveniently may be taken from the textbooks mentioned before.

Step (b) of the process enables one to generate complex oligo- or polysaccharide structures on the mono- or oligosaccharide grafted material surfaces obtained according to step ($a_1$) or ($a_2$) by applying one or more different carbohydrates, in particular one or more different monosaccharides, in the presence of one or more different glycosyltransferases. In case of different carbohydrates to be attached, the enzymes may be applied sequentially one-by-one or as combinations of several enzymes, together with the corresponding enzyme substrate in each case. Depending on the nature of the terminal sugar radicals present on the modified surface obtained according to step ($a_1$) or ($a_2$), the enzymes elongate the carbohydrate structure on the material surface in accordance with the specifity of the enzymes and the substrates present in the reaction mixture.

The modified material surfaces obtained according to step (b) of the process may be purified afterwards applying conventional techniques such as for example washing or extraction with a solvent like water, methanol, ethanol and the like. The characterization of the surfaces obtained may be performed by various techniques including X-ray Photoelectron Spectroscopy (XPS) or Time Of flight Secondary Ion Mass Spectrometry (TOF-SIMS).

A further embodiment of the invention is a material comprising a carbohydrate structure on its surface obtainable by the process as outlined above.

The materials obtained according to the process of the invention are useful, for example, for the manufacture of biomedical devices. Examples of suitable biomedical devices are wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

Biomedical devices made of a material according to the invention have a variety of unexpected advantages over those of the prior art which make those devices very suitable for practical purposes. For example, they do have a very pronounced biocompatibility including a high surface wettability, blood compatibility and tissue integration. Biomedical devices such as renal dialysis membranes, blood storage bags, pacemaker leads or vascular grafts made of materials of the invention resist fouling by proteins by virtue of the continuous layer of bound water, thus reducing the rate and extent of thrombosis. Blood-contacting devices fabricated according to the present invention are therefore haemocompatible and biocompatible.

The invention in a further embodiment relates to a biosensor for the detection of carbohydrate related interactions, for example, with biocomponents of fluids in living organisms or with cells comprising a surface which is modified by a process according to the invention. The biosensor comprises, for example, an optical chip the surface of which is patterned with an array of oligosaccharides or polysaccharides according to the process of the invention. Preferably, oligo- or polysaccharides differing in their carbohydrate composition are patterned in specific shapes on the chip surface, for example in hexagonal shape. The detection of oligo- or polysaccharide related interactions may be based on refractive index changes as used in integrated optical detection.

The biosensor according to the present invention may be used in any area involving carbohydrate interactions, for example, for the detection of carbohydrate binding molecules, functionally active biomolecules or parts thereof, e.g. pathogens, toxins, enzymes, hormons, blood factors;

for the detection of carbohydrate binding molecules associated with infectious biosystems, e.g. bacteria, viruses, parasites;

EXAMPLE 1

Synthesis of N-[m-[3-(trifluoromethyl)diazirin-3-yl]
phenyl]-4-(-3-thio(-1-D-galactopyranosyl)-
succinimidyl)butyramide (MAD-Gal)

1-thio-b-galactopyranose (1.5 mg) is dissolved in 150 μl of buffer A (20 mM citric acid, 35 mM $Na_2HPO_4$, 108 mM NaCl, 1 mM ethylenediamine-tetraacetic acid (EDTA)) and 150 μl of ethanol, N-(m-(3-trifluoromethyl)diazirine-3-yl) phenyl)-4-maleimido-butyramide (MAD, 3.3 mg, preparation according to A. Collioud et al., Bioconjugate Chemistry 4, 528–536 (1993)) is dissolved in 150 μl of ethanol and an additional 150 μl of buffer A. Both solutions are mixed. The mixture is stirred and allowed to react at room temperature for 90 min, to give the compound MAD-Gal. The product is purified by HPLC. The HPLC flow rate is 2 ml/min. For gradient elution (0 min.-100% A; 5 min.-100% A; 20 min.-70% A; 30 min.-0% A; 40 min. 0%A), solvent B is added to solvent A (solvent A, 0.1% TFA in water; solvent B, 0.1% TFA in acetonitrile/water (4:1 by volume)). Detection is performed at 254 nm and fractions of the eluant are collected. $^{13}$C.NMR ($D_2O$ chemical shift (δ) in parts per million): 179.14, 178.40, 177.99, 177.86, 173.30, 137.79, 129.53, 129.38, 122.43, 121.84, 118.32, 84.42, 84.27, 78.99, 78.91, 73.84, 73.66, 69.73, 69.68, 68.58, 68.49, 60.80, 60.69, 39.61, 38.66, 38.46, 37.71, 35.83, 33.57, 22.68, 22.57 ppm. Mass Calc (M–H): 561.1 Da/e, found: 561.1 Da/e.

EXAMPLE 2

Immobilization of MAD-Gal on diamond) Hot filament deposited thin-film diamond is used as the substrate to exploit MAD-Gal immobilization. Pristine samples (5×5 mm) are washed (5 min ultrasonic bath in hexane and in ethanol) and dried for 2 hours at room temperature under vacuum (Å 6 mbar). Then, MAD-Gal (10 μl 0.25 mM in ethanol) is deposited as a droplet released from a syringe. The samples are dried for 2 hours at room temperature under vacuum (30–40 mbar). They are irradiated for 20 min with the Stratalinker right source (0.95 mW/cm$^2$) and washed by ultrasound treatment twice in ethanol (5 min) and twice in hexane (5 min). Patterning was performed with a mask consisting of 40 μm×40 μm square windows separated by 40 μm bridges. MAD-Gal was deposited on the diamond surface before mask-assisted illumination and final washing.

EXAMPLE 3a (Synthesis of 6-mercaptohexanoic acid) A 500 cm$^3$ round bottom flask equipped with a magnetic stirrer is charged with ε-caprolactone (13.6 g, 120 mmol), thiourea (8.4 g, 110 mmol) and hydrobromic acid 48% (98 g, 120 mmol). The reaction mixture is heated (~120° C.) in an oil bath for 9 hours, cooled to room temperature. Sodium hydroxide solution (50% m/v) is added until clearance. This solution is further heated (~100° C.) for 3 hours, cooled to room temperature and acidified with sulphuric acid (aqueous solution 50% v/v) until a clear solution appears (pH~1). The clear solution is extracted with diethyl ether (3×100 cm$^3$). The combined organic phase is washed with water (3×100 cm$^3$), dried ($MgSO_4$) and the solvent is evaporated under reduced pressure. The remaining yellow oil is purified by distillation under reduced (135–140° C., ~1 mm Hg) to give a colourless oil (3.76 g). Chemical shift $δ_H$(250 MHz; $CDCl_3$) are 1.34 (1H, t, J 7.9, SH), 1.37–1.51 (m, 2H, $CH_2$), 1.57–1.71 (4H, m, 2×$CH_2$), 2.37 (2H, t, J 7.3, $CH_2COOH$), 2.53 (2H, dt, J 7.9, 7.0, $HSCH_2$), 10.4 (1H, br, COOH); $δ_C$ (62.90 MHz; $CDCl_3$) 23.92, 24.21, 27.56, 33.41 ($HSCH_2$), 33.75 ($CH_2COOH$), 179.92 (COOH); m/z (+Cl) 166 ([M+$NH_4$]+, 1.7%), 148 ([M]$^+$, 0.8). 130 (2.8), 115 (2.8), 102 (3 5).

EXAMPLE 3b

Synthesis of 5-carboxypentyl-(2,3,4,6-tetra-O-
acetyl-β-D-galactopyranosyl)-(1→4)-2,3,6-tri-O-
acetyl-1-thio-β-D-glucopyranoside A two necked round bottom flask is charged with 2.72 g (4 mmol) of lactose octaacetate, 0.48 g of 6-mercaptohexanoic acid (3.2 mmol) and dry $CH_2Cl_2$ (10 ml). $BF_3$ diethyletherate is added dropwise (0.85 g, 6 mmol). The reaction is allowed to proceed for 2 hours at room temperature under nitrogen. The mixture is diluted with $CH_2Cl_2$ (200 ml) and sequentially washed with 1 M HCl (3 times 100 ml) and water (1 time 100 ml). The organic phase is dried over $MgSO_4$, and the solvent is evaporated at reduced pressure to give a yellow oil. Purification requires two runs by flash chromatography ($CH_2Cl_2$:MeOH 20:1 and 10:1). It yields to 5-carboxypentyl-(2,3,4,6-tetra-O-acetyl-b-D-galactopyranosyl)-(1→4)-2,3,6-tri-O-acetyl-1-thio-b-D-glucopyranoside (1.65 mg, 67%). $δ_H$(250 MHz; $CDCl_3$) 1.34–1.46 (2H, m, $CH_2$), 1.54–1.67 (4H, m, 2×$CH_2$), 1.96 (3H, s, $COCH_3$), 2.02 (3H, s, $COCH_3$), 2.03 (6H, s, $COCH_3$), 2.04 (3H, S, $COCH_3$), 2.09 (3H, s, $COCH_3$), 2.13 (3H, s, $COCH_3$), 2.32 (2H, t, J 7.4, $CH_2$), 2.54–2.68 (2H, m, $CH_2$), 3.58–3.61 (1H, m, C-5'), 3.75 (1H, t, J 9.4, C-4'), 3.85 (1H, t, J 6.6, G-5), 3.98–4.19 (m, 3H, C-6 and C-6b'), 4.44 (1H, d, J 92, C-1), 4.84–4.96 (2H, m), 5.07 (1H, dd, J 6.2), 5.18 (1H, t, J 9.4, C-4'), 5.32 (1H, d), $d_C$ (62.90 MHz; $CDCl_3$) 20.37, 20.50, 20.61, 20.71, 23.96, 27.89, 29.17, 33.54, 60.68, 62.13, 66.49, 68.95, 70.15, 70.53, 70.85, 73.83, 76.04, 83.35 (C-1), 100.91 (C-1'), 169.01 ($COCH_3$), 169.59 ($COCH_3$), 169.68 ($COCH_3$), 170.07 ($COCH_3$), 170.30 ($COCH_3$, 178.35 ($CH_2COH$). IR 1665 cm$^{-1}$.

EXAMPLE 3c

Synthesis of 5-carboxypentyl N-[m-[3-
(trifluoromethyl)diazirin-3-yl]phenyl(2,3,4,6-tetra-
O-acetyl-b-D-galactopyranosyl)-(1→4)-2,3,6-tri-O-
acetyl-1-thio-b-D-glucopyranoside N-formyl m-[3-(trifluoromethyl)diazirine-3-yl]aniline (120 mg) is dissolved in 3 ml of methanol. Concentrated HCl (1 ml) is added. The mixture is reacted for 10 min at ambient temperature. The reaction mixture is cooled to 0° C. in an ice bath and neutralised with NaOH (3 ml, 6N). The aqueous phase is extracted with ethyl ether (5 times 4 ml). The combined organic phase is washed with deionised water (5 ml) and dried over $MgSO_4$. The solvent is evaporated under reduced pressure to give a yellow oil m-[3-(trifluoromethyl)-diazirine-3-yl]aniline.

A round bottom flask is charged with 383 mg of 5-carboxypentyl-(2,3,4,6-tetra-O-acetyl-β-D-galactopyranosyl)-(1→4)-2,3,6-tri-O-acetyl-1-thio-b-D-glucopyranoside from Example 3b in 9 ml of dry DMF. The solution is placed under nitrogen and cooled to −20° C. in a salt-ice bath. Triethylamine (209 μl) is added dropwise. The mixture is further cooled at −60° C. in a dry ice/acetone bath. Ethyl chloroformate (80 μl in 1.1 ml of dry DMF) is added. The reaction is allowed to proceed for 30 minutes. The deprotected m-[3-(trifluoromethyl)-diazirine-3-yl]aniline dissolved in 1.1 ml of DMF is added dropwise. The mixture is allowed to stand for 5 hours and 35 minutes at room temperature. A separating funnel is charged with 40 ml of 1 M NaCl and ice. The reaction mixture is poured into the separating funnel and extracted with diethyl ether (4 times 15 ml). The combined organic phase is washed sequentially with HCl 1 M (2 times 10 ml), and saturated $NaHCO_3$ (2 times 10 ml) and deionised water (2 times 10 ml). The organic phase is then dried over $MgSO_4$. The solvent is evaporated under reduced pressure to give an oil. The oil is further purified by flash chromatography (1.5×16 cm) on silica gel 60 (0.015–0.04 mm). It is eluted with a 1/1 AcOEt/Hex (200 ml). The desired product (71 mg) has an rf of 0.1 (1/1 AcOEt/Hex). $δ_H$(200 MHz; $CDCl_3$) 1.37–1.54 (2H, m, $CH_2$), 1.54–1.85 (4H, m, 2×$CH_2$), 1.96 (3H, s, $COCH_3$), 2.03 (3H, s, $COCH_3$), 2.04 (3H, s, $COCH_3$), 2.05 (3H, s, $COCH_3$), 2.06 (3H, s, $COCH_3$), 2.13 (3H, s, $COCH_3$), 2.15 (3H, s, $COCH_3$), 2.34 (2H, t, J 6.9, $CH_2$), 2.54–2.72 (2H, m, $CH_2$), 3.58–3.68 (1H, m, C-5'), 3.81 (1H, t, J 9.4, C-4'), 3.87 (1H, t, J 6.6, C-5), 4.00–4.22 (m, 3H, C-6 and C-6b'), 4.44 (1H, m, C-1), 4.88–5.02 (2H, m), 5.15 (1H, m), 5.21 (1H, m), 5.32 (1H, d), 7.08 (1H, m), 7.3 (1H, m), 7.5 (2H, m, aromatic). $δ_C$ (50.3 MHz; $CDCl_3$) in ppm: 20.51, 20.63, 20.79, 20.96, 24.78, 27.74, 29.21, 29.81, 37.28, 60.76, 61.96, 66.61, 69.17, 70.22, 7.75, 70.98, 73.77, 76.07, 76.39, 76.81, 77.03, 77.66, 83.66 (C-1), 101.07 (C-1'), 117.36, 120.75, 121.89, 129.63, 129.92, 138.90, 168.99 ($COCH_3$), 1659.67 ($COCH_3$), 169.87 ($COCH_3$), 170.07 ($COCH_3$), 170.13 ($COCH_3$), 170.34 ($COCH_3$), 170.72 ($COCH_3$), 171.43 (O=C—N). MS ESI: calc: 948.26 m/z, exp: 948.20 m/z, additional peaks at 822 (M–H–3 Ac), 780 (M–H–4 Ac), 738 m/z (M–H–5 Ac).

EXAMPLE 3d

Synthesis of 5-carboxamidopentyl N-[m-[3-(trifluoromethyl)diazirin-3-yl]phenyl β-D-galactopyranosyl)-(1→4)-1-thio-β-D-glucopyranoside (lactose aryl diazirine)

In a round bottom flask, 71 mg of 5-carboxypentyl N-[m-[3-(trifluoromethyl)diazirin-3-yl]phenyl(2,3,4,6-tetra-O-acetyl-β-D-galactopyranosyl)-(1→4)-2,3,6-tri-O-acetyl-1-thio-β-D-glucopyranoside according to Example 3c is dissolved in 8 ml of dry methanol. The solution is put under a nitrogen atmosphere. Sodium methoxide (0.6 ml, 0.12 mM, 0.6 equivalents) is added dropwise. The reaction is allowed to proceed for 9 hours.

The mixture is neutralised with Amberlyt 15, and filtered over Celite. The organic solvent is then evaporated under reduced pressure to give the desired lactose aryl diazirine.

$δ_H$(200 MHz; $MeOH-d_4$) 1.49–1.69 (2, m, $CH_2$), 1.69–1.89 (4.6, m, 2×$CH_2$), 2.46 (2, t, J 7.2, $CH_2$) 2.73–2.95 (2, m, $CH_2$), 3.44–4.09 (12, m, carbohydrate, methanol), 4.39 (1, d, C-1'), 6.94–7.16 (1, m, aromatic), 7.39–7.55 (1, m, aromatic), 7.64–7.76 (2, m, aromatic), $d_C$ (50.3 MHz; $MeOH-d_4$) in ppm 26.25, 29.35, 30.70, 30.75, 37.80, 62.06, 62.5, 64.43, 70.30, 72.54, 72.86, 74.10, 74.83, 77.09, 77.94, 80.5, 87.08, 105.04, 118.63, 122.20, 122.65, 130.73. Quaternary carbons ($CF_3$, C=O, Caro-N, Caro-C) are note observed due to the low signal/noise ratio. MS ESI (M−1): calc: 654.19 m/z, found: 654.16 m/z. IR 1660 $cm^{-1}$.

EXAMPLE 4

Immobilization of Lactose Aryl Diazirine on Diamond and Polystyrene

Immobilisation of 5-carboxamidopentyl N-[m-[3-(trifluoromethyl)diazirin-3-yl]phenyl β-D-galactopyranosyl)-(1→4)-1-thio-β-D-glucopyranoside is explored with diamond and polystyrene (PS). Pristine diamond surfaces are washed (5 min ultrasonic bath in hexane and then in ethanol, Uvasol) and dried for 2 hours at room temperature under vacuum (Å 6 mbar). Polystyrene is used without washing prior to the deposition. A solution of 5-carboxamidopentyl N-[m-[3-(trifluoromethyl)diazirin-3-yl]phenyl β-D-galactopyranosyl)-(1→4)thio-β-D-glucopyranoside (0.25 mM in methanol, HPLC grade) is spotted with a syringe. The deposited volumes of the solution are given in Table 1 below.

TABLE 1

| Sample | area in $mm^2$ | Deposited volume in μl |
|---|---|---|
| Diamond | 25 | 10 |
| Polystyrene | 50 | 25 |

The samples are dried for 2 hours at room temperature under vacuum (30–40 mbar). They are irradiated for 25 min at 350 nm with the Stratalinker light source (0.95 $mW/cm^2$) and washed. Diamond samples are washed as follows: ultrasonic bath three times with methanol (HPLC grade, 5 min) and once with hexane (Uvasol, 5 min). The polystyrene samples are washed four times with water (HPLC grade).

EXAMPLE 5

(Enzymatic transfer of sialic acid) Lactose aryl diazirine is immobilised on ELISA title plates according to the procedure of Example 4 except that 45 μl of the lactose aryl diazirine are used. The wells are washed 4 times 5 minutes with deionised water after light irradiation. Sialic acid incorporation is performed with recombinant a-2,6-sialyl transferase (*Pichia pastoris* $K_m$ 158 μM in PBS at 37° C. with CMP-NANA (CMP-N-acetylneuramic acid), 4.65 mM with LacNAc, 64 μU/μl). $^{14}$C. Radiolabelled CMP-NANA (Amersham) is used to probe the enzymatic reaction. The sialic add is labelled at positions 4, 5, 6, 7 and 9. Its specific radioactivity is 370 kBq/400 μl (10.8 GBq/mmole. 10 μCi/400 μl, 85 pmole/μl). Incubation conditions are described in the following Table 2.

TABLE 2

| incubation condition of a-2,6-sialyl transferase | | | | |
|---|---|---|---|---|
| Number | $H_2O$ μl | Caco Buffer (μl) 1M, pH 6.8 | Transferase (μl) | CMP-[$^{14}$C]-NANA (μl) | Incubation time (min) |
| 1 | 34 | 5 | 20 | 1 | 360 |
| 2 | 34 | 5 | 20 | 1 | 360 |
| 3 | 34 | 5 | 20 | 1 | 0 |
| 4 | 34 | 5 | 20 | 1 | 120 |
| 5 | 34 | 5 | 20 | 1 | 240 |
| 6 | 34 | 5 | 20 | 1 | 360 |
| 7 | 44 | 5 | 0 | 1 | 360 |

The reaction is stopped with 100 μl of cold water (0° C.), The wells are then sequentially wished four times with water. The polystyrene wells are placed in polyethylene radioactivity measurements vessels and dissolved in toluene. Two ELISA wells are measured per scintillation vial. The incorporation yield is from 5 to 50% after 6 hours with a surface density in the order of $10^{12}$ to $10^{13}$ molecules/$cm^3$.

What is claimed is:

1. A process for the preparation of a carbohydrate structure on a material surface comprising the steps of:

($a_1$) photochemically fixing one or more different compounds of formula

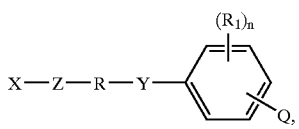

onto the material surface,
wherein X is the radical of a mono- or oligosaccharide,
R is a divalent organic radical having from 2 to 30 C-atoms which may be further substituted,
Z is —O—, —S— or a direct bond,
Y is a functional group linking R to the aromatic ring,
$R_1$ is an electron-withdrawing substituent and n is an integer from 0 to 4,
Q is a radical of formula

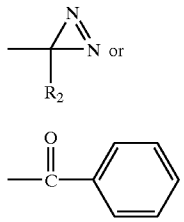

and $R_2$ is an electron-withdrawing substituent; or
($a_2$) photochemically fixing a compound of formula

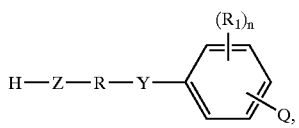

wherein R, $R_1$, n, Y, Z and Q are as defined above, onto the material surface and subsequently converting the —ZH groups to —Z—X moieties, wherein X has the above meaning; and (b) enzymatically attaching one or more further carbohydrate to the X radicals of the modified surface obtained according to step ($a_1$) or ($a_2$).

2. A process according to claim 1, comprising steps ($a_1$) and (b).

3. A process according to claim 1, wherein X is the radical of mono-, di-, tri- or tetrasaccharide.

4. A process according to claim 3, wherein X is the radical of a galactose, lactose mannose, N-acetyl glucosamine, N-acetyl galactosamine or N-acetyl lactosamine.

5. A process according to claim 1, wherein R is linear or branched $C_2$–$C_{24}$-alkylene, which may be interrupted by —O— or —$NR_3$—, and $R_3$ is hydrogen or $C_1$–$C_4$-alkyl.

6. A process according to claim 1, wherein Y is a group —C(O)O—, —OC(O)—, —C(O)$NR_4$—, —$NR_4$C(O)—, —OC(O)—NH—, —NHC(S)NH— or —NHC(O)NH—, and $R_4$ is hydrogen or $C_1$–$C_4$-alkyl.

7. A process according to claim 1, wherein $R_1$ is fluorine and n is an integer from 0 to 4.

8. A process according to claim 1, wherein Q is a radical of formula (2a), and $R_2$ is trifluoromethyl.

9. A process according to claim 1, wherein in step (b) the carbohydrate(s) are attached to the radicals X by means of a glycosyl transferase or a mixture of different glycosyl transferases.

10. A process according to claim 1, wherein a monosaccharide or a mixture of different monosaccharides or a derivative thereof is attached to the X radicals in step (b).

11. A process according to claim 1, wherein sialic acid is attached to the X radicals by means of a sialyl transferase in step (b).

12. A process according to claim 3, wherein X is the radical of a mono- or disaccharide.

13. A process according to claim 12, wherein X is the radical of a disaccharide.

14. A process according to claim 5, wherein R is linear $C_4$–$C_{18}$-alkylene.

15. A process according to claim 14, wherein R is linear $C_6$–$C_{10}$-alkylene.

16. A process according to claim 7, wherein n is 0.

* * * * *